United States Patent
Haerle et al.

(10) Patent No.: US 10,420,928 B2
(45) Date of Patent: Sep. 24, 2019

(54) IMPLANTABLE MEDICAL DEVICE HAVING A SCHEME FOR MANAGING STORAGE OF DATA

(71) Applicant: Medtronic, Inc., Minneapolis, MN (US)

(72) Inventors: Mark L Haerle, Bloomington, MN (US); Robert D Musto, Champlin, MN (US); Paul G Wassmund, Linwood, MN (US)

(73) Assignee: Medtronic, Inc., Minneapolis, MN (US)

( * ) Notice: Subject to any disclaimer, the term of this patent is extended or adjusted under 35 U.S.C. 154(b) by 207 days.

(21) Appl. No.: 15/375,722

(22) Filed: Dec. 12, 2016

(65) Prior Publication Data

US 2017/0165469 A1    Jun. 15, 2017

Related U.S. Application Data

(60) Provisional application No. 62/267,064, filed on Dec. 14, 2015.

(51) Int. Cl.
| | |
|---|---|
| *A61N 1/02* | (2006.01) |
| *A61N 1/362* | (2006.01) |
| *A61N 1/372* | (2006.01) |
| *G06F 12/02* | (2006.01) |
| *G16H 10/60* | (2018.01) |

(52) U.S. Cl.
CPC ............ *A61N 1/025* (2013.01); *A61N 1/362* (2013.01); *A61N 1/37252* (2013.01); *A61N 1/37264* (2013.01); *G06F 12/0246* (2013.01); *G16H 10/60* (2018.01); *G06F 2212/1028* (2013.01); *G06F 2212/1036* (2013.01); *G06F 2212/7207* (2013.01); *G06F 2212/7209* (2013.01); *Y02D 10/13* (2018.01)

(58) Field of Classification Search
USPC .......................................................... 607/30
See application file for complete search history.

(56) References Cited

U.S. PATENT DOCUMENTS

| | | | |
|---|---|---|---|
| 4,357,943 | A | 11/1982 | Thompson et al. |
| 4,476,868 | A | 10/1984 | Thompson |
| 5,052,388 | A | 10/1991 | Sivula et al. |
| 5,896,393 | A | 4/1999 | Yard et al. |
| 6,104,638 | A | 8/2000 | Larner et al. |

(Continued)

OTHER PUBLICATIONS (PCT/US2016/066331) PCT Notification of Transmittal of the International Search Report and the Written Opinion of the International Searching Authority, dated Mar. 9, 2017, 11 pages.

*Primary Examiner* — Nicole F Lavert

(57) ABSTRACT

The disclosure describes a scheme for managing the operations of a flash memory. The scheme enables the flash memory to be used in a write-once mode to allow non-volatile storage of small amounts of data that must be written repeatedly. Among other things, the scheme eliminates the need to erase sectors of the flash memory, thus eliminating the high current consumption associated with erasures, while enabling preservation of relevant data in those sectors. In the context of an implantable medical device, this scheme is used to store data that is needed after a reset of the device, such as MRI-related data that is/are dynamically adjusted by firmware, or program code updates.

48 Claims, 8 Drawing Sheets

(56) References Cited

U.S. PATENT DOCUMENTS

| | | |
|---|---|---|
| 7,130,240 B2 | 10/2006 | Chae et al. |
| 7,613,871 B2 | 11/2009 | Tanaka et al. |
| 7,779,426 B2 | 8/2010 | Rogers et al. |
| 8,879,319 B1 | 11/2014 | Cassuto et al. |
| 2002/0091417 A1* | 7/2002 | Splett .................... A61N 1/362 607/30 |
| 2010/0250840 A1 | 9/2010 | Wong |
| 2010/0293320 A1 | 11/2010 | Li et al. |

* cited by examiner

IMPLANTABLE MEDICAL DEVICE HAVING A SCHEME FOR MANAGING STORAGE OF DATA

CROSS-REFERENCE TO RELATED APPLICATIONS

This application claims the benefit of U.S. Provisional Application No. 62/267,064, filed on Dec. 14, 2015. The disclosure of the above application is incorporated herein by reference in its entirety.

FIELD

The present invention relates to implantable medical devices, and more specifically, to a scheme for managing storage of data in the implantable medical devices.

BACKGROUND

Implantable medical devices exist that monitor, and/or electrically stimulate body tissue for treatment or relieving the symptoms of a wide variety of physiological or psychological maladies. Such implantable devices are typically part of systems that are entirely implantable within the patient or are partially implantable and partially external to the patient.

Such implantable devices are often powered by an internal power source, such as a battery, that powers the device functions continuously over a long period of time. Often for implantable medical devices, the power source used to power the device's circuitry is non-rechargeable. As such, the longevity of the device is a function of the rate of depletion of the battery, which may range from approximately three years to approximately ten years based upon the usage of the stored charge.

The implantable devices will typically also comprise electronic circuitry that includes one or more memory components. One example of such a memory component is a flash memory. Flash memories have emerged in the art in recent years as an important nonvolatile memory which combines the advantages of EPROM density with EEPROM electrical eraseability. Flash memories are so named because a plurality of memory cells in a block or sector are erased at the same time. Thereafter, selected bits, bytes, or words are programmed into the memory. Flash memories have been used to store executable code and/or other types of information. Flash memory can be rewritten and can hold its contents without power, and thus is nonvolatile. Flash memory is generally constructed of flash memory cells where, generally, single bits of data are stored in and read from respective memory cells. The cells are generally programmed by hot electron injection and erased by Fowler-Nordheim tunneling or other mechanisms.

The erase, program, and read operations are commonly performed by application of appropriate voltages to certain terminals of the memory cell. In an erase or write operation, the voltages are applied so as to cause a charge to be removed or stored in the memory cell. In a read operation, appropriate voltages are applied so as to cause a current to flow in the cell, wherein the amount of such current is indicative of the value of the data stored in the cell. The memory device includes appropriate circuitry to sense the resulting cell current in order to determine the data stored therein, which is then provided to data bus terminals of the device for access by other devices in a system in which the memory device is employed.

Programming circuitry controls a bit of a cell by applying a signal to a wordline, which acts as a control gate, and changing bitline connections such that the bit is stored by the source and drain connections. Programming a cell using a suitable mechanism, such as hot electron injection, generally increases the threshold voltage of a cell. Erasing is performed as a blanket operation wherein an array or sector of cells can be simultaneously erased and typically produces a lower threshold voltage in the cell.

In the blanket erasing of flash memory, cells within an array or sector are typically erased concurrently. After each erase pulse, an erase verification or read can be performed to determine if each cell in the array is now "erased" (blank), or yet remains "un-erased" or "under-erased", (e.g., whether the cell has a threshold voltage above a predetermined limit). If an under-erased cell is detected, an additional erase pulse can be applied to the entire array until all cells are sufficiently erased. U.S. Pat. No. 7,130,240 discloses a method for erasing sectors of a flash memory in sequence. However, erasing the contents of memory is a time-consuming and current-draining process.

In the context of an implantable medical device, the erase operations may consume a substantial portion of the battery power that is available over the operating life of the device. Moreover, because the erasure requires that an entire sector be erased, the existing erasure methods do not cater for selective erasure of unwanted data that is stored in a given sector if the given sector also contains wanted data. Therefore, a need remains for memory management techniques that optimize the consumption of the charge stored by the power source to extend the device longevity.

SUMMARY

The disclosure describes a scheme for managing the operations of a flash memory. The scheme enables the flash memory to be used in a write-once mode to allow nonvolatile storage of small amounts of data that must be written repeatedly.

Among other things, the scheme eliminates the need to erase sectors of the flash memory, thus eliminating the high current consumption associated with erasures, while enabling preservation of relevant data in those sectors. In the context of an implantable medical device, this scheme is used to store data that is needed after a reset of the device, such as MRI-related data that is/are dynamically adjusted by firmware, or program code updates.

BRIEF DESCRIPTION OF THE DRAWINGS

The following drawings are illustrative of particular embodiments of the present disclosure and therefore do not limit the scope of the disclosure. The drawings are not to scale (unless so stated) and are intended for use in conjunction with the explanations in the following detailed description. Embodiments will hereinafter be described in conjunction with the appended drawings wherein like numerals/letters denote like elements, and.

DETAILED DESCRIPTION OF DRAWINGS

The disclosure is described in conjunction with the application of an implantable medical device ("IMD") that includes electronics having a combination of ultra-low power micro-electronic circuits and a low-power microcontroller to obtain the desired combination of flexibility and longevity. However, it should be understood that the inventive concepts may be applied to any other electronic devices.

Within the IMD, there are many discrete processes involving collecting, storing, and presenting physiologic trends of a patient, as well as in delivering therapies (e.g., a cardiac therapy). The battery located within the IMD provides the power necessary for performing such operations. The components utilized for performing each of the various operations draw a preset amount of power from the finite source battery to perform the IMD's intended operation. Therefore, conserving battery power can provide for longer, uninterrupted operation of the IMD. Many IMDs include some type of data storage component including volatile memory components (e.g., static/dynamic random access memory) or nonvolatile memory components (e.g., electrically erasable programmable read-only memories and flash memories) that consume energy from the battery to power the read, write, or erase operations of the memory component.

The disclosure describes a scheme for managing the operations of a flash memory. The scheme enables the flash memory to be used in a write-once mode to allow nonvolatile storage of small amounts of data that must be written repeatedly. Among other things, the scheme eliminates the need to erase sectors of the flash memory, thus eliminating the high current consumption associated with erasures, while enabling preservation of relevant data in those sectors. In the context of an implantable medical device, this scheme is used to store data that is needed after a reset of the device, such as MRI-related data that is/are dynamically adjusted by firmware, or program code updates. As used in this disclosure, the term "data" refers to information, parameters, program or executable code, and/or any other unit or aggregate of energy or signals that contain some meaning or usefulness. Such data may be used to control the operations and functionality of the IMD.

Figure 1:
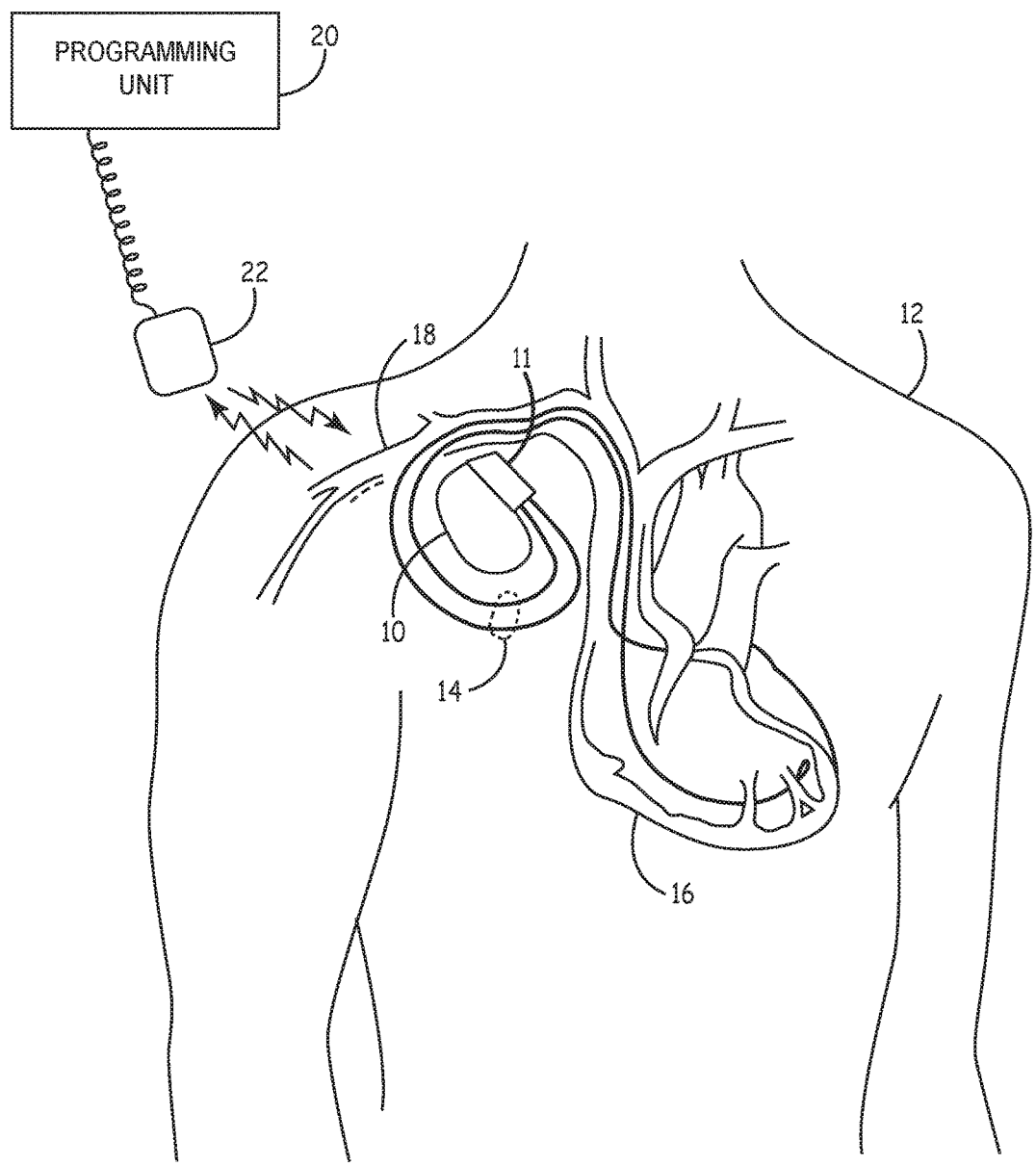
FIG. 1 illustrates an implantable medical system that includes an exemplary implantable medical device.

FIG. 1 illustrates an implantable medical system, which includes, for example, an implantable medical device ("IMD") 10 that has been implanted in a patient 12. The IMD 10 is housed within a hermetically sealed, biologically inert outer canister or housing, which may itself be conductive so as to serve as an electrode in the pacing/sensing circuit. One or more leads, collectively identified with reference numeral 14 are electrically coupled to the IMD 10 in a conventional manner and extend into the patient's heart 16 via a vein 18. Disposed generally near a distal end of the leads 14 are one or more conductive electrodes for receiving electrical cardiac signals or delivering electrical pacing stimuli to the heart 16. The leads 14 may be implanted with their distal end situated in either the atrium or ventricle of the heart 16. Although the disclosure is described herein in an embodiment that includes a cardiac device, it may be advantageously embodied in numerous other types of implantable medical systems in which it is desirable to optimize the energy consumption of an implanted device with a finite energy source.

With continued reference to FIG. 1, an external programming unit 20 is depicted for non-invasive communication with the IMD 10 via conventional uplink and downlink communication channels, which are not described in greater detail herein so as to avoid unnecessarily obscuring the details of the present disclosure. In an embodiment, the programming unit 20 may be associated with a programming head 22, in accordance with conventional medical device programming systems, for facilitating two-way communication between the IMD 10 and the programmer 20. In many known implantable systems, the programming head 22, such as that depicted in FIG. 1, is positioned on the patient's body over the implant site of the device 10 (usually within about 2 to about 3 inches, or equivalently, about 5 to about 8 cm, of skin contact), such that one or more antennas within the head 22 can send radio frequency (RF) signals to, and receive radio frequency (RF) signals from, an antenna (not shown) disposed within the hermetic enclosure of the implanted device 10 or disposed within a connector block 11 of the device 10, in accordance with common practice in the art. Other communication schemes, such as proprietary short and long-range telemetry, radiofrequency, and Bluetooth® wireless communication, may be utilized that eliminate the need for programming head 22.

Figure 2:
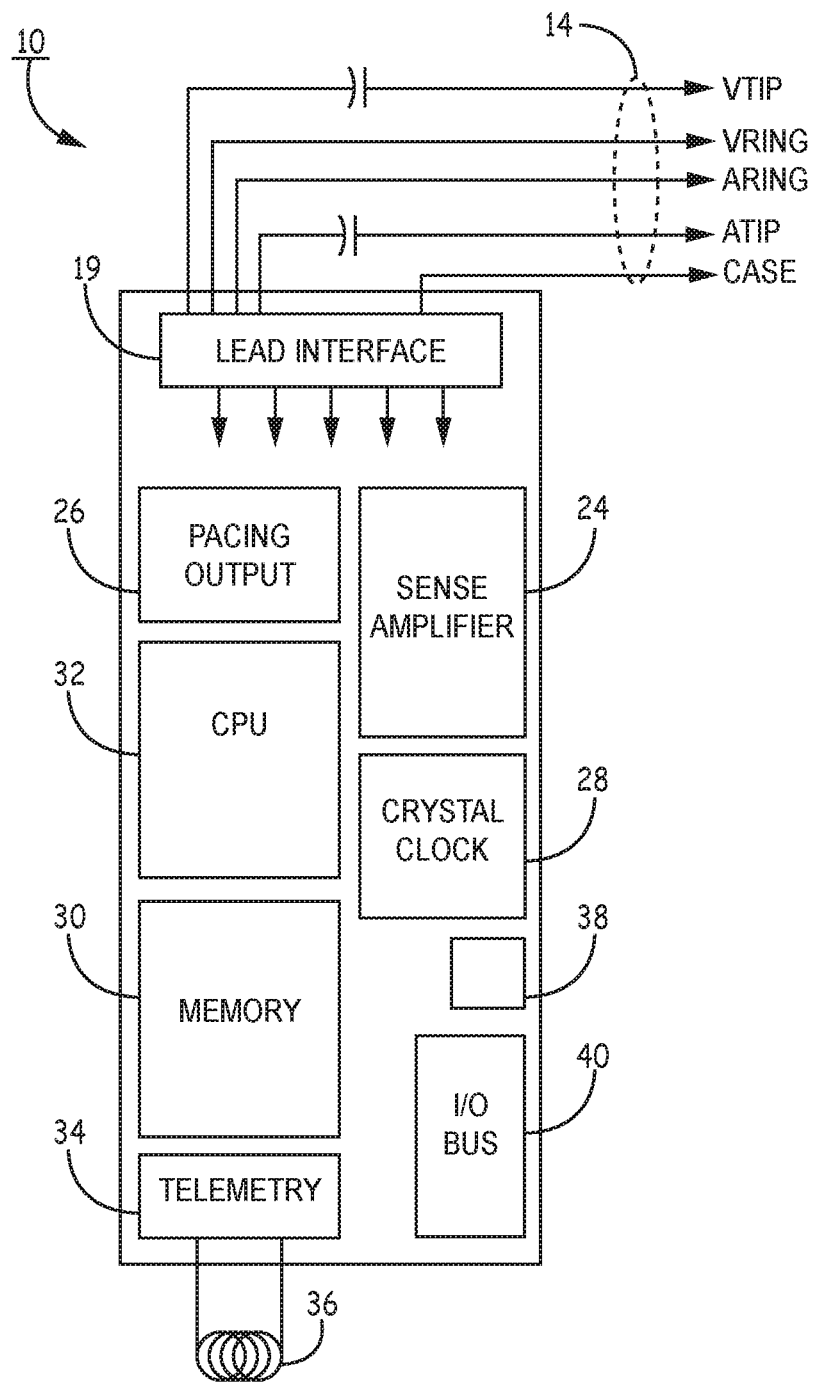
FIG. 2 shows a general block diagram of electronic circuitry that makes up the implantable medical device.

FIG. 2 provides a general block diagram of electronic circuitry that makes up the IMD 10. The IMD 10 is a device capable of performing a variety of functions, such as delivering electrical stimulation therapy to the patient 12 in accordance with the presently disclosed embodiment of the disclosure. FIG. 2 shows that IMD 10 comprises circuitry for controlling the device's pacing and sensing functions. Aspects of the IMD circuitry may be of conventional design, in accordance for example, with what is disclosed in U.S. Pat. No. 5,052,388 issued to Sivula et al. and entitled "Method and Apparatus for Implementing Activity Sensing in a Pulse Generator."

To the extent that certain components of the circuitry of the IMD 10 are conventional in their design and operation, such components will not be described herein in detail because it is believed that design and implementation of such components would be a matter of routine practice to those of ordinary skill in the art. For example, the circuitry of the IMD 10 shown in FIG. 2 includes sense amplifier circuitry 24, stimulating pulse output circuitry 26, a crystal clock 28, a memory unit 30, and a pacing timing and control circuit in the form of a programmed microprocessor 32.

The IMD 10 also includes an internal telemetry communications circuit 34 coupled to an antenna 36 so that it is capable of communicating with the external programming unit 20. Various telemetry systems for providing the uplink and downlink communication channels between the external programming unit 20 and the IMD 10 have been shown in the art and may be employed herein without departing from the spirit and scope of the disclosure.

Memory unit 30 may comprise a non-transitory computer-readable storage medium, including any volatile, non-volatile, magnetic, optical, or electrical media, such as a random access memory (RAM), read-only memory (ROM), nonvolatile RAM (NVRAM), electrically-erasable programmable ROM (EEPROM), flash memory, or any other digital or analog storage media.

With continued reference to FIG. 2, the IMD 10 is coupled to one or more leads 14 which, when implanted, extend transvenously between the implant site of the IMD 10 and the patient's heart 16, as previously noted with reference to FIG. 1. Physically, the connections between the leads 14 and the various internal components of the IMD 10 are facilitated by a conventional connector block assembly 11, shown in FIG. 1. Electrically, the coupling of the leads 14 and the internal electrical components of the IMD 10 may be facilitated by a lead interface circuit 19, which functions, in a multiplexer-like manner, to selectively and dynamically establish necessary connections between various conductors in the leads 14, including, for example, atrial tip and ring electrode conductors ATIP and ARING and ventricular tip and ring electrode conductors VTIP and VRING, and individual electrical components of the IMD 10, as would be familiar to those of ordinary skill in the art. For the sake of clarity, the specific connections between the leads 14 and the various components of the IMD 10 are not shown in FIG. 2, although it will be clear to those of ordinary skill in the art that, for example, the leads 14 will necessarily be coupled, either directly or indirectly, to sense amplifier circuitry 24 and stimulating pulse output circuitry 26, in accordance with common practice, such that cardiac electrical signals may be conveyed to the sense amplifier circuitry 24, and such that stimulating pulses may be delivered to cardiac tissue, via the leads 14.

It will be appreciated that the signals received over the leads 14 by the sense amplifier circuitry 24 may be collected and stored in the memory unit 30 by the microprocessor 32 acting under control of software also stored in the memory unit 30. Additional data, such as the timing of signals delivered by the stimulating pulse output circuitry 26 may also be stored in the memory unit 30. This stored data may be later retrieved and delivered to the programming unit 20 via the telemetry communications circuit 34.

As previously noted, the circuitry of the IMD 10 includes the microprocessor 32 which may be an off-the-shelf programmable microprocessor or microcontroller, but in the presently illustrated embodiment of the disclosure is a custom integrated circuit. Microprocessor 32 may include any one or more of a microprocessor, a controller, a digital signal processor (DSP), an application specific integrated circuit (ASIC), a field-programmable gate array (FPGA), or equivalent discrete or integrated logic circuitry. In some examples, microprocessor 32 may include multiple components, such as any combination of one or more microprocessors, one or more controllers, one or more DSPs, one or more ASICs, or one or more FPGAs, as well as other discrete or integrated logic circuitry. The functions attributed to microprocessor 32 in this disclosure may be embodied as software, firmware, hardware or any combination thereof. While the embodiment of FIG. 2 refers to a digital signal processor-based architecture, it should be noted that other architectures, such as the logic or state machine architectures or other components or circuitry for performing a processing function, are contemplated in the present disclosure. Such architectures are not discussed in detail herein merely for the sake of brevity.

In one embodiment, clock 28 in the presently illustrated embodiment is a crystal controlled oscillator that provides a main timing clock signal ($F_O$). In another embodiment, the clock 28 may include a clock generator such as a crystal oscillator for providing a first clock signal of one frequency ($F_O$) and a programmable frequency divider for generating multiple clock signals of different frequencies from the first clock signal and for outputting one of the multiple clock signals ($F_1$-$F_n$). Again, the signal lines over which the aforementioned clock signals are provided to the various components of the IMD 10 (e.g., the microprocessor 32) are omitted from FIG. 2 for the sake of clarity. It is believed that those of ordinary skill in the art will be familiar with such an operative arrangement.

It is to be understood that the various components of the IMD 10 depicted in FIG. 2 are powered by means of a battery 38, which is contained within the hermetic enclosure of the IMD 10, in accordance with common practice in the art. For the sake of clarity in the drawings, the connections between the battery and the other components of the IMD 10 are not shown.

Those of ordinary skill in the art will appreciate that the IMD 10 may include numerous other components and subsystems, for example, activity sensors and associated circuitry. The presence or absence of such additional components in the IMD 10, however, is not believed to be directly pertinent to the disclosure, which relates generally to optimizing operation of the microcontroller to minimize power consumption and promote an extension of the life of the energy source.

Stimulating pulse output circuitry 26, which functions to generate cardiac stimuli under control of signals issued by the microprocessor 32, may be, for example, of the type disclosed in U.S. Pat. No. 4,476,868 to Thompson, entitled "Body Stimulator Output Circuit." Again, however, it is believed that those of ordinary skill in the art could select from among many various types of prior art pacing output circuits, which would be suitable for the purposes of practicing the disclosure. The sense amplifier circuitry 24, may be, for example, of the type disclosed in U.S. Pat. No. 4,357,943 to Thompson, entitled "Demand Cardiac Pacemaker Having Reduced Polarity Disparity."

Generally, the sense amplifier circuitry 24 functions to receive electrical cardiac signals from the leads 14 and to process such signals to derive event signals reflecting the occurrence of specific cardiac electrical events, including atrial contractions (P-waves) and ventricular contractions (R-waves). These event-indicating signals are provided to the microprocessor 32 for use by the microprocessor 32 in controlling the synchronous stimulating operations of the IMD 10 in accordance with common practice in the art. In addition, these event-indicating signals, as discussed above, may be communicated, via the uplink communication channel, to the external programming unit 20 for storage and visual display to a physician or clinician.

It is important to note that leadless embodiments of the present disclosure are also contemplated, where one or more stimulation and/or sensing electrode capsules or modules are implanted at or near a desired target tissue site, and the capsules or modules deliver electrical stimuli directly to the site using a preprogrammed stimulation regime, and/or the capsules or modules sense electrical or other pertinent signals.

Figure 3:
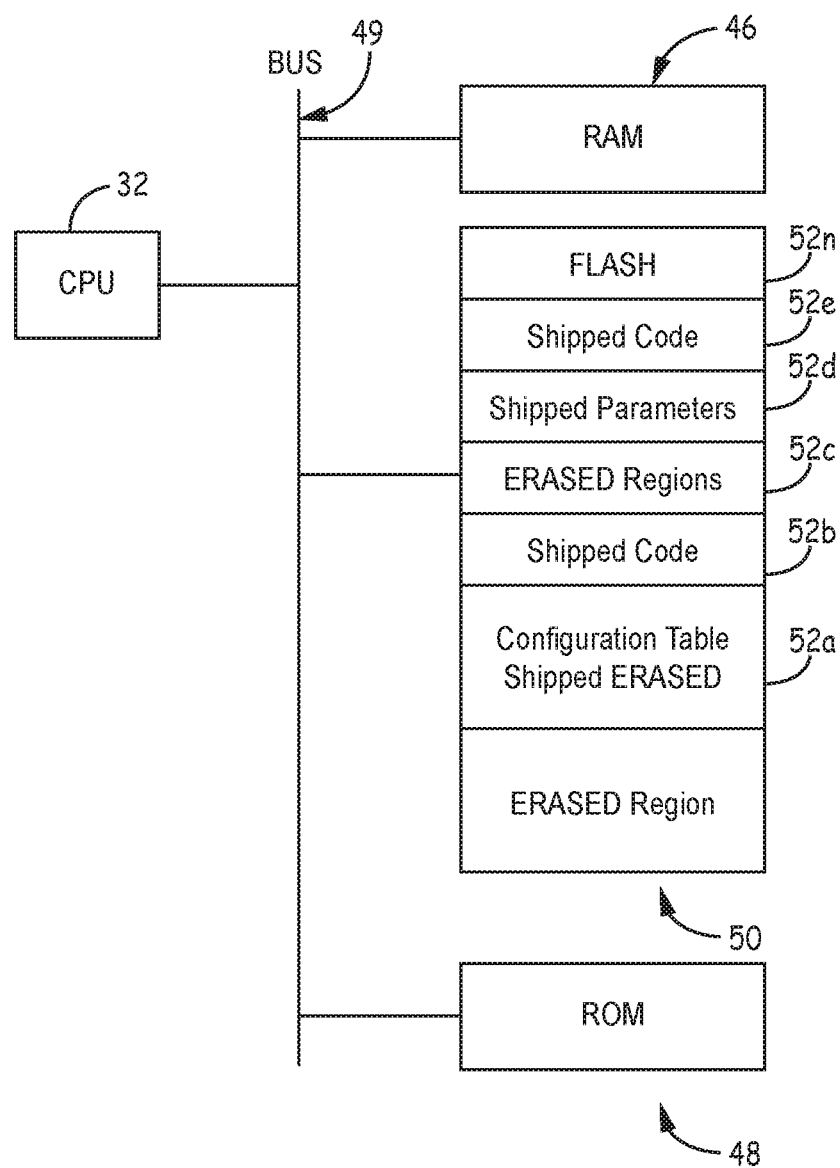
FIG. 3 shows a block diagram illustrating a memory unit coupled to a microprocessor.

Referring now to FIG. 3, there is shown a block diagram illustrating a memory unit coupled to a microprocessor. Specifically, the memory unit 30 depicted includes a random access memory (RAM) 46, a read only memory (ROM) 48, and a flash memory device 50. As will be described in more detail with reference to FIGS. 4-8, the flash memory 50 is operated in accordance with embodiments of this disclosure. The microprocessor is electrically coupled to the flash memory 50, the RAM 46, and ROM 48 via a data/address bus 49 for access of data stored therein. The bus 49 serves to transmit data or signals between the various components of system IMD electronic circuitry. The bus 49 can be any suitable physical or logical means of connecting computer systems and components. This includes, but is not limited to, direct hard-wired connections, fiber optics, infrared and wireless bus technologies.

The flash memory 50 is generally divided into a plurality of segments that are commonly referred to as sectors 52a-52n (collectively "sectors 52"). Each of the plurality of sectors 52 includes multiple flash cells. The microprocessor 32 may allocate one or more regions 54 within one or more of the sectors 52 for storage of data. In one embodiment, the one or more regions 54 may have variable sizes (i.e., each region 54 may have a non-uniform number of flash memory cells). In another embodiment, one or more sectors 52 may be configured having one or more regions 54 that have the same size, or a uniform number of flash memory cells. The memory cells can include NAND cells, or NOR cells, or a combination of the two.

Prior to programming, the flash memory 50 may be prepared to store data by clearing each of the sectors 52. In one embodiment, the clearing operation of the flash memory 50 may be performed by Fowler-Nordheim tunneling or any other mechanisms known in the art to set all bits in each sector 52 (or regions 54) to binary digit 1. The clearing operation may be performed, for example, during the manufacturing of the flash memory 50 components.

Figure 4:
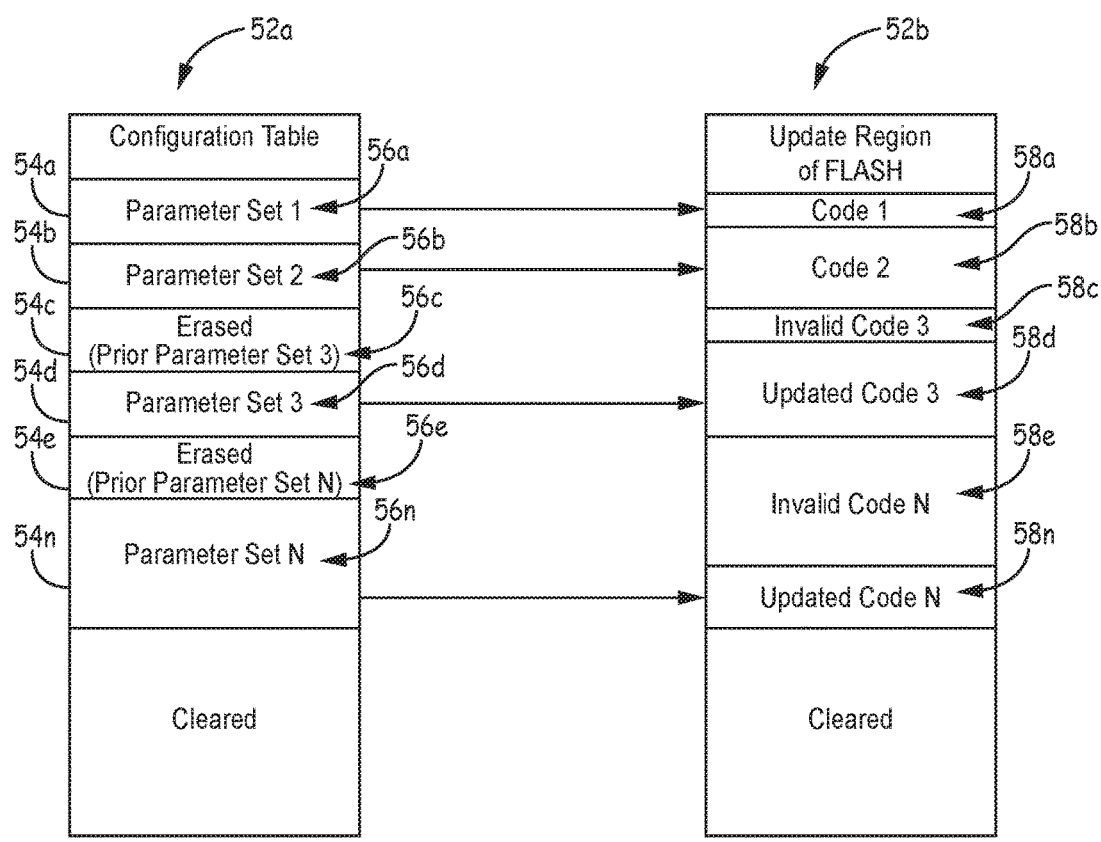
FIG. 4 depicts a diagram illustrating a physical arrangement of a flash memory device.

FIG. 4 depicts a diagram illustrating a physical arrangement of a flash memory device. The flash memory 50 includes a plurality of sectors 52 that may have uniform sizes or variable sizes. Each of the sectors 52 may be partitioned into one or more regions 54a-n (collectively "regions 54"). A region may comprise a location for storage of one or more individually addressable array of data 56a-56n, with the array of data being, for example, a parameter or a program code.

In the illustrative embodiment, the regions 54 are shown having differing sizes. However, it should be understood that each of the regions may preferentially be formed having the same size.

For simplicity, the one or more of the sectors 52 may be conceptualized as being allocated for storage of a configuration table. Each region 54 will contain an array of data that is a single entry in the configuration table. Stated otherwise, such a configuration table may be utilized to store one or more parameters, each of which is associated with discrete code that is stored in other sections of the memory 50. The plurality of arrays of data are stored sequentially into the sector 52. In other words, the arrays of data are stored in a logical sequence, or consecutively arranged, that corresponds to the sequence in which the microprocessor 32 will access the regions 54. The arrays of data are written into the designated sector(s) 52 until the sector(s) is/are full.

In one embodiment, the plurality of arrays of data 56 are parameters that include address pointers to individual program codes 58. For instance, the array of data 56a will include an address of the location of the program code 58a which is enabled, the array of data 56b will include an address of the location of the program code 58b which is enabled, the array of data 56c will include an address of the location of the program code 58c which is disabled, the array of data 56d will include an address of the location of the program code 58d which is enabled and contains the updates to the data 56c, the array of data 56e will include an address of the location of the program code 58e which is disabled, array of data 56n will include an address pointer of the location of the program code 58n which is enabled and contains the updates to the data 56e, and so on and so forth. The program codes 58 may comprise software that is to be executed by the microprocessor 32. Accordingly, the microprocessor 32 will execute a method to access each of the arrays of data 56 and execute the program code 58 at the address indicated by the pointer.

As will be described in more detail with reference to FIG. 8, each array of data 56a-n includes an identifier that designates the corresponding program code 58a-n as being valid or invalid. The microprocessor 32 initially evaluates the identifier to determine whether to jump to the program code 58 at the address indicated by the pointer and only proceeds to execute that corresponding program code 58 if the identifier indicates that the array of data is enabled. An array of data containing valid data is denoted by a state flag that is programmed or set to an enabled state. In other words, the enabled state indicates that the first array of data is active and programmed with current operative data. However, if the identifier indicates that the array of data is disabled, then the microprocessor skips, or does nothing, that array of proceeds to evaluate the identifier of the next array of data. The invalid array of data is denoted by the state flag being set to a disabled state to indicate that the data in the first array of data is inactive and therefore should not be acted upon.

Figure 5:
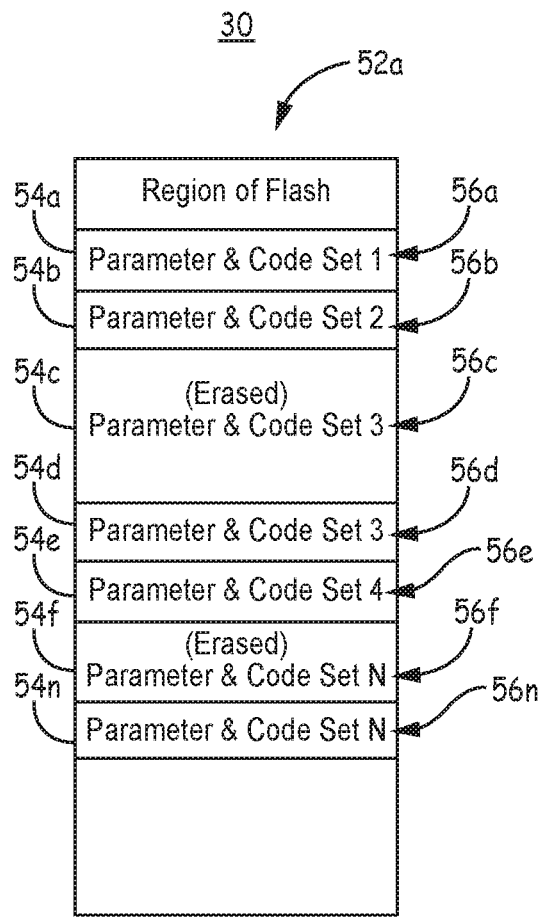
FIG. 5 depicts another diagram illustrating a physical arrangement of a flash memory device.

FIG. 5 depicts another diagram illustrating a physical arrangement of a flash memory device. The flash memory 50 of FIG. 5 includes a plurality of sectors 52 that may have uniform sizes or variable sizes. Each of the sectors 52 may be partitioned into one or more regions 54. A region may comprise a location for storage of one or more individually addressable array of data 56a-56n, with the array of data being, for example, a parameter and/or a program code.

In the illustrative embodiment, the regions 54 are shown having differing sizes. However, it should be understood that each of the regions may preferentially be formed having the same size.

For simplicity, the one or more sectors 52 may be conceptualized as being allocated for storage of an array of data that combines a single entry of a configuration table with a single discrete program code. The plurality of arrays of data is stored sequentially into the sector 52. In other words, the arrays of data are consecutively arranged or stored in a logical sequence that corresponds to the sequence in which the microprocessor 32 will access the regions 54. The arrays of data are written into the sector(s) 52 until the sector(s) is full.

In one embodiment, each array of data 56 will include a parameter and discrete program code 58. The parameter will include identifier information, while the program code 58 may comprise software that is to be executed by the microprocessor 32. Accordingly, the microprocessor 32 will execute a method to access each of the arrays of data 56 and execute the program code 58 based on a value of the identifier information. Therefore, unlike the embodiment of FIG. 4, the parameter need not include an address for the location of the program code since each entry includes both the identifier and the code.

As will be described in more detail with respect to FIG. 8, the identifier designates the corresponding program code 58a-n as being valid or invalid. The microprocessor 32 initially evaluates the identifier to determine whether to execute the program code 58 associated with the array of data and only proceeds to execute that corresponding program code 58 if the identifier indicates that the array of data is active. An active array of data is denoted by a state flag that is set to an enabled state. However, if the identifier indicates that the array of data is inactive, then the microprocessor proceeds to evaluate the identifier of the next array of data.

Figure 6:
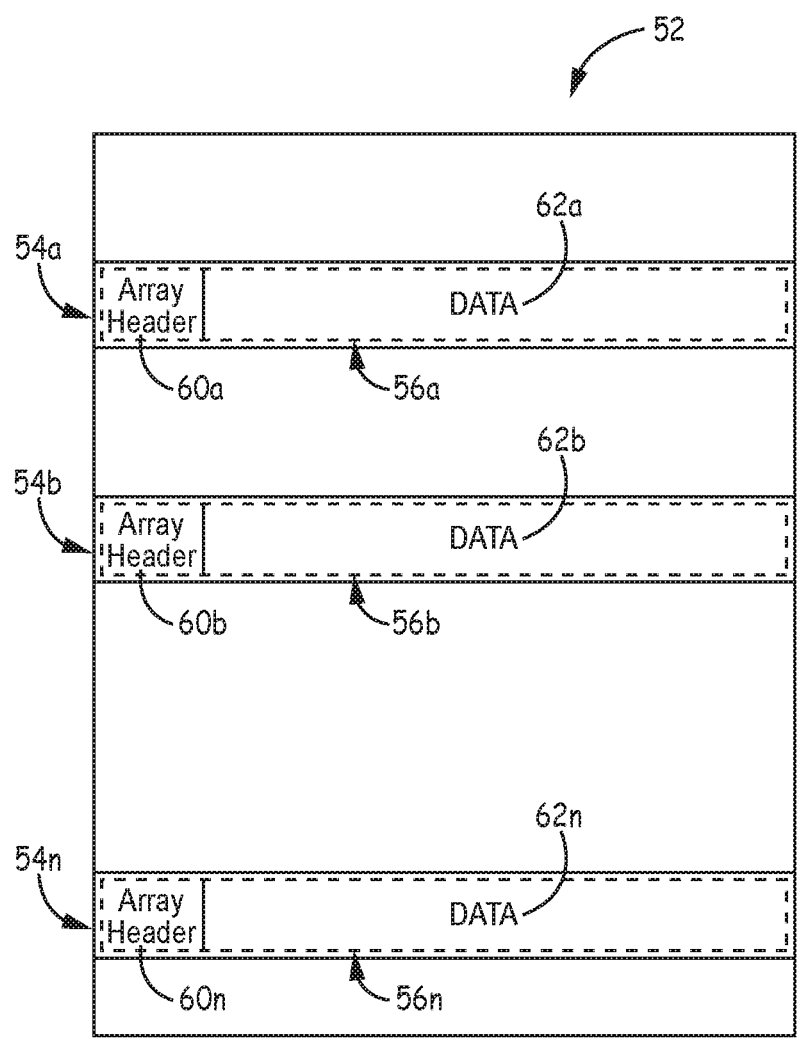
FIG. 6 depicts an array of data 56 as written into a region 54 within a sector 52 of the flash memory device 50 in accordance with an embodiment.

FIG. 6 depicts an array of data 56 as written into a region 54 within a sector 52 of the flash memory device 50 in accordance with an embodiment. In accordance with embodiments of the present disclosure, each array of data 56 includes an identifier that designates the received array of data as being the most recent array of data. In one embodiment, the identifier may be a header 60 of the array of data.

In the depicted embodiment, the header 60 may comprise any desired predetermined size such as one or more bits, bytes or words. For example, the header 60 may be two (2) bits. The header 60 also includes a flag that is configured in a predetermined binary digit format, such as having one or more bits, bytes or words in accordance with embodiments of the disclosure. The information stored within the flag designates the array of data 56 as either being active or inactive. For example, if the flag is set to "11" in binary digits, the array of data is invalid and the region is completely erased and ready to be written into. The flag would be set in this manner in a scenario where, for example, the memory component has been initialized (which may include erasing the entire memory or specific regions) prior to beginning the IMD operation or the memory component has been erased upon filling up the available space or under certain predetermined events. Continuing with the example, if the flag is set to "01" in binary digits, then the array of data 56 is valid and contains programmed data. The flag would be set in this manner in a scenario where, for example, an individual sector in the memory component has been programmed with current operational data to be accessed and read by the microprocessor. Finally, in the example, if the flag is set to "00" in binary digits, the array of data is invalid and contains written data. The flag would be set in this manner in a scenario where, for example, the data in an individual sector in the memory component is invalid and is therefore disabled to prevent further access and use of that data.

It some embodiments, other types of information may be stored in the header 60 of the array of data 56 as is conventionally known in the art. For example, information about the length of the array of data 56, error correction codes and any other information may also be stored in the header 60.

As will be discussed in conjunction with FIG. 6, each array of data 56 also includes data. In accordance with embodiments of the present disclosure, the data 62 in the array of data 56 may include a parameter as discussed in conjunction with FIG. 4 or program code and/or data as discussed in conjunction with FIG. 5.

In the present invention, a valid status identifier represents the operational data. For example, if the array of data 56 refers to a program code update, then the operational program code will be designated by the enabled flag. In other words, the enabled flag points to the operational program code which is the most recent program code. During execution of method/routine/process tasks, the microprocessor 50 (FIG. 3) will evaluate the identifier to determine whether the array of data is valid or invalid. If valid, the microprocessor will read, retrieve and/or execute the entry and proceed to the address at the pointer (FIG. 4) or execute the corresponding code (FIG. 5).

Figure 7:
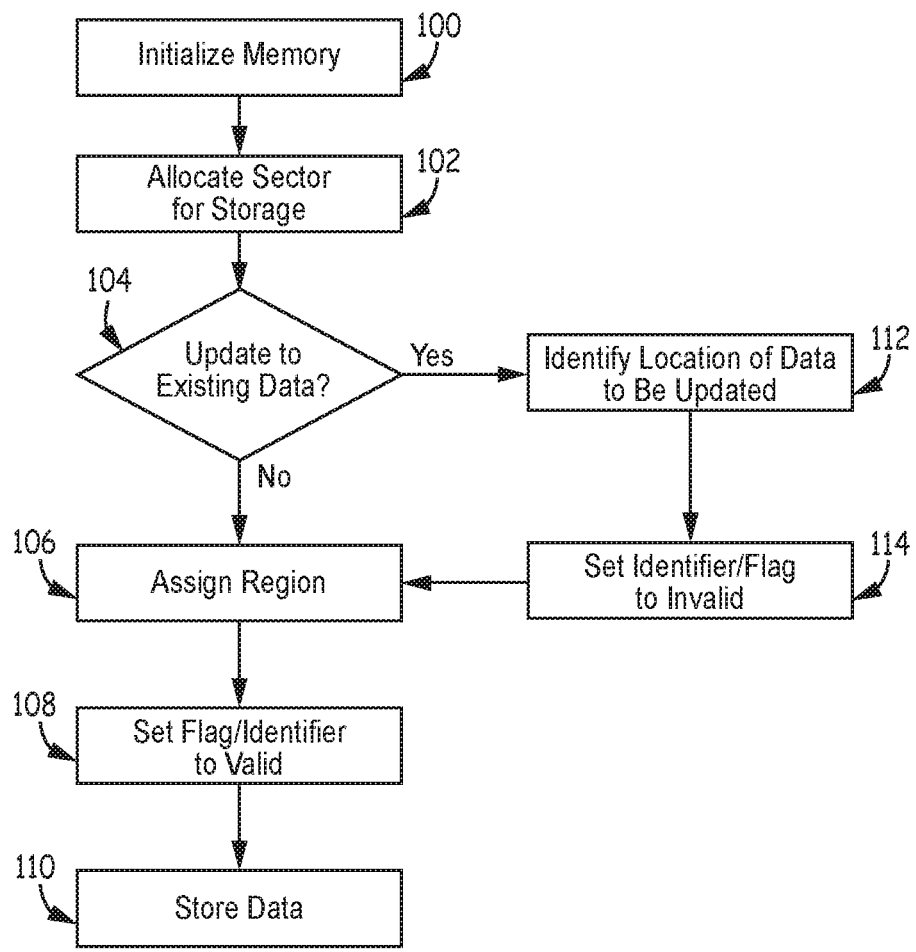
FIG. 7 is a flowchart illustrating a method for managing data in a flash memory array in accordance with embodiments of the present disclosure.

FIG. 7 is a flowchart illustrating a method for managing data in a flash memory array in accordance with embodiments of the present disclosure. The reader may refer to the foregoing figures in conjunction with the description of FIG. 7. In one embodiment, the method may be implemented as a data management module that comprises computer readable instructions that are stored in memory unit 30 and executed by a processor such as microprocessor 32.

At task 100, the flash memory device 50 is initialized by clearing at least one if not all of the plurality of sectors 52 of the flash memory 50. In one embodiment, the one or more sectors 52 may be designated for storing a particular type of data that includes parameters that may occasionally need to be updated. The designated memory sectors are written to in a write-once mode, with each data entry occupying a small amount of space on the sector. In the context of an implantable medical device, this scheme can be used to, for example, store data that is needed after a reset of the device, such as MRI-related data that is/are dynamically adjusted by firmware, or code updates. The data, or updates, may be received from an external device such as programming unit 20 through telemetry communications circuit 34.

The initialization may be performed during the manufacturing of the flash memory 50 or prior to an initial use of the memory. In other words, the clearing process may involve erasing the contents of the flash memory cells in the designated sectors 52 such that no data is stored in those designated sectors 52. In accordance with one embodiment, all bits in each region of the designated sectors 52 may be set to binary digit 1 by erasing the sectors. The data in each cleared region will include a header that contains a "cleared" state flag. The cleared state flag will denote the cleared region as having no valid data stored therein to be read and, therefore, as a region that can be written to.

Subsequent to initializing the memory 50, one of the plurality of sectors 52 may be allocated for storage of a configuration table at task 102. The configuration table will generally include one of more parameters that may include pointers to other regions or sectors 52 of the flash memory 50. For example, the configuration table will include a given parameter that is dynamically adjusted by firmware such that each successive update of the given parameter will be stored sequentially in the configuration table.

Responsive to receiving a first array of data, the microprocessor 32 will determine whether the data is an update of existing data or whether the data is new data at task 104.

If the received first array of data is a new data, then the microprocessor 32 will assign a received array of data to a region of the designated sector 52 at task 106. The assigned region corresponds to a next available entry in the configuration table. For example, if the received array of data is a first array, then the region will correspond to the first available region in the designated sector 52. The received array of data may comprise a parameter including an address pointer for a program code that is stored in some other location within the flash memory 50. The microprocessor 32 may retrieve the parameter to determine which code should be executed during operation of the IMD. Alternatively, the array of data may comprise the identifier and program code to be executed by the microprocessor.

At task 108, an identifier of each array of data is set to designate the array of data as being active. In accordance with embodiments of the present disclosure, each array of data includes a flag that is set to designate the array of data as being active or inactive. The microprocessor 32 will set the flag in the received array of data into an enabled state.

The array of data is transmitted through the bus 49 for storage in a first or a next consecutive region at task 110. For simplicity, the regions within the designated sector may be understood as being sequentially ordered. This sequential order may correspond to a logical flow through which the microprocessor, while executing a method, will access the arrays of data stored in the designated sector.

Returning to task 104, if the received first array of data is an update to an existing array of data, the microprocessor 32 will determine which existing array of data is being updated at task 112. At task 114, the flag of the existing array of data that is to be updated (or has been updated) will be changed from an enabled state to a disabled state. However, the existing array of data will not be erased.

Each array of data that is received after the first array of data will be assigned to a corresponding next region of the designated sector 52 at task 106. For example, a second array of data will be assigned to a second consecutive region, a third array of data will be assigned to a third consecutive region, and so on and so forth. The arrays of data may be stored in sequential regions of the designated sector 52 or in any other manner, provided the microprocessor 32 can sequentially loop through each array of data in the order of reception.

As such, the method described in conjunction with FIG. 7 may be implemented to store a plurality of arrays of data. The identifier of each of the arrays of data is used during the execution of a method by the microprocessor 32 to determine which arrays of data are active and which arrays of data are inactive. This enables the microprocessor 32 to read, retrieve and/or execute each of the active arrays of data in a sequential manner (consecutively from an active array of data to a subsequent active array of data) while skipping (or not reading, retrieving, or executing) any inactive array(s) of data. The plurality of arrays of data is written into the designated sector(s) 52 until the sector(s) are full.

By implementing the foregoing memory management scheme, a flash memory sector may be designated for storage of data that requires frequent updates without having to erase the contents of the entire sector when some of the data becomes inactive or outdated due to an update.

Figure 8:
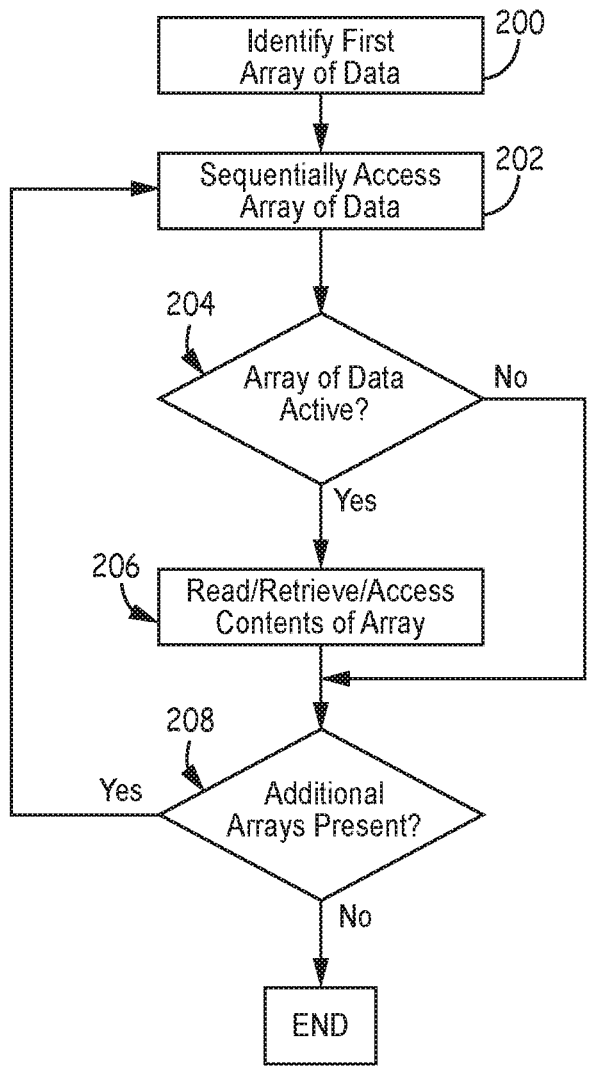
FIG. 8 depicts a flow chart showing an exemplary method for implementing a flash memory in accordance with embodiments of the present disclosure.

FIG. 8 depicts a flow chart showing an exemplary method for implementing a flash memory in accordance with embodiments of the present disclosure. The reader may refer to the foregoing FIGS. 1-6 in conjunction with the description of FIG. 8. In one embodiment, the method may be implemented as a data management module that comprises computer readable instructions that are stored in memory unit 30 and executed by a processor such as microprocessor 32.

As described herein, arrays of data are stored within a flash memory 50. The microprocessor 32 may access the arrays of data, for example, following a device reset in order to restart the functions of the IMD 10. The method will begin by identifying a first array of data in a designated sector and read the header of the first array of data at task 200.

Subsequent to identifying the first array of data, the microprocessor 32 will, beginning with the first array, sequentially access the contents of the arrays of data at task 202. Each of the arrays of data will contain a header that designates the status of the corresponding array of data as either being active or inactive.

At task 204, the microprocessor 32 determines whether the identified array of data is active or inactive. In accordance with embodiments of this disclosure, the determination of whether an array of data is active or inactive is made based on the contents of the flag contained in the header.

If the array of data is active, the microprocessor 32 will read, retrieve and/or execute the contents of the contents of the array of data at task 206. The contents may include a parameter pointing to an address of program code that is to be executed or to yet another parameter. Additionally or alternatively, the contents may include program code to be executed by the microprocessor 32.

Returning to task 204, if the array of data was determined to be inactive and/or after completing the execution of the code associated with the active array of data, the microprocessor 32 determines whether there are any subsequent arrays of data at task 208. If there is no additional array of data, the microprocessor 32 concludes the method. Otherwise, the microprocessor 32 loops back to task 202 to access the next consecutive array of data.

Providing software, firmware and hardware to accomplish the present invention, given the disclosure herein, is within the abilities of one of skill in the art. For the sake of brevity, conventional techniques related to ventricular/atrial pressure sensing, IMD signal processing, telemetry, and other functional aspects of the systems (and the individual operating components of the systems) may not be described in detail herein. The connecting lines shown in the various figures contained herein are intended to represent example functional relationships and/or physical couplings between the various elements. It should be noted that many alternative or additional functional relationships or physical connections may be present in an embodiment of the subject matter.

The description refers to elements or nodes or features being "connected" or "coupled" together. As used herein, unless expressly stated otherwise, "connected" means that one element/node/feature is directly joined to (or directly communicates with) another element/node/feature, and not necessarily mechanically. Likewise, unless expressly stated otherwise, "coupled" means that one element/node/feature is directly or indirectly joined to (or directly or indirectly communicates with) another element/node/feature, and not necessarily mechanically. Thus, although the schematics shown in the figures depict exemplary arrangements of elements, additional intervening elements, devices, features, or components may be present in an embodiment of the depicted subject matter.

While the disclosure is susceptible to various modifications and alternative forms, specific embodiments thereof have been shown by way of example in the drawings and are herein described in detail. It should be understood, however, that the description herein of specific embodiments is not intended to limit the disclosure to the particular forms disclosed, but on the contrary, the intention is to cover all modifications, equivalents, and alternatives falling within the spirit and scope of the disclosure as defined by the appended claims.

What is claimed is:

1. An implantable medical device, comprising:
   a microprocessor;
   a flash memory array having a plurality of sectors, wherein each of the sectors includes a plurality of regions; and
   a data management module comprising instructions which, when executed, by the microprocessor cause the microprocessor to:
   assign a received first array of data to a first of the plurality of regions of a given one of the sectors;
   store the first array of data in the assigned first region;
   set a flag in the first array of data to an enabled state; and
   modify the content of the flag from the enabled state to a disabled state without erasing the first region in response to a subsequent receipt of a command to update the data in the first array.

2. The implantable medical device of claim 1, wherein the microprocessor accesses the first array of data responsive to the flag being set to the enabled state.

3. The implantable medical device of claim 1, further comprising instructions that, when executed by the microprocessor, cause the microprocessor to:
assign a subsequently received array of data to a subsequent plurality of regions;
store the subsequently received array of data in the assigned data region; and
set a flag in the subsequently received array of data to an enabled state.

4. The implantable medical device of claim 3, further comprising instructions that, when executed by the microprocessor, cause the microprocessor to allocate one or more regions of the one or more sectors for storage of each of the received first and subsequent arrays of data.

5. The implantable medical device of claim 3, wherein the microprocessor evaluates a value of the flag in each of the first or subsequent arrays of data responsive to a memory read request, and one of: reads the data stored within any one of the arrays of data in the given sector based on the flag being set to the enabled state, and skips the data stored within any one of the arrays of data in the given sector based on a value of the flag being set to the disabled state.

6. The implantable medical device of claim 3, further comprising instructions that, when executed by the microprocessor, cause the microprocessor to set the flag of each of the plurality of sectors to a cleared state to designate each sector as not being programmed prior to storage of the first or subsequent arrays of data in each corresponding sector.

7. The implantable medical device of claim 1, further comprising instructions that, when executed by the microprocessor, cause the microprocessor to sequentially access currently operative arrays of data in the given sector, wherein the valid arrays of data are determined based on the flag being set to an enabled state.

8. The implantable medical device of claim 1, wherein the first array of data comprises an address to at least one of a parameter, an executable code, and data stored within the plurality of sectors.

9. The implantable medical device of claim 8, further comprising instructions that, when executed by the microprocessor, cause the microprocessor to execute the executable code stored within the plurality of sectors.

10. The implantable medical device of claim 1, wherein each of the arrays of data includes a header and the flag is contained in the header.

11. The implantable medical device of claim 1, wherein each of the regions comprises a uniform number of flash memory cells.

12. The implantable medical device of claim 1, wherein each of the regions comprises a non-uniform number of flash memory cells.

13. The implantable medical device of claim 1, wherein at least one of the sectors comprises logically sequential regions.

14. The implantable medical device of claim 13, wherein the microprocessor assigns the received first array of data to a first of the logically sequential regions.

15. The implantable medical device of claim 1, wherein the flash memory array comprises at least one of NAND and NOR flash memory cells.

16. The implantable medical device of claim 1, wherein each sector of the flash memory is configured for a single write, determined based on a status of the flag on each of the regions within the sector.

17. The implantable medical device of claim 1, wherein the first array of data comprises an address to at least one of a parameter, an executable code, and data stored within the plurality of sectors.

18. An implantable medical device, comprising:
a microprocessor;
a flash memory array having a plurality of sectors, wherein each of the sectors includes a plurality of regions; and
a data management module comprising instructions which, when executed, by the microprocessor cause the microprocessor to:
assign a received first array of data to a first of the plurality of regions of a given one of the sectors;
store the first array of data in the assigned first region;
set a flag in the first array of data to an enabled state; and
modify the content of the flag from the enabled state to a disabled state without erasing the first region in response to a subsequent receipt of a command to update the data in the first array; and
wherein the flag being set to the enabled state indicates that the first array of data is programmed with current operative data, and the flag being set to the disabled state indicates that the first array of data is programmed with inactive data.

19. The implantable medical device of claim 18, wherein the microprocessor accesses the first array of data responsive to the flag being set to the enabled state.

20. The implantable medical device of claim 18, further comprising instructions that, when executed by the microprocessor, cause the microprocessor to:
assign a subsequently received array of data to a subsequent plurality of regions;
store the subsequently received array of data in the assigned data region; and
set a flag in the subsequently received array of data to an enabled state.

21. The implantable medical device of claim 18, further comprising instructions that, when executed by the microprocessor, cause the microprocessor to allocate one or more regions of the one or more sectors for storage of each of the received first and subsequent arrays of data.

22. The implantable medical device of claim 21, wherein the microprocessor evaluates a value of the flag in each of the first or subsequent arrays of data responsive to a memory read request, and one of: reads the data stored within any one of the arrays of data in the given sector based on the flag being set to the enabled state, and skips the data stored within any one of the arrays of data in the given sector based on a value of the flag being set to the disabled state.

23. The implantable medical device of claim 21, further comprising instructions that, when executed by the microprocessor, cause the microprocessor to set the flag of each of the plurality of sectors to a cleared state to designate each sector as not being programmed prior to storage of the first or subsequent arrays of data in each corresponding sector.

24. The implantable medical device of claim 18, further comprising instructions that, when executed by the microprocessor, cause the microprocessor to sequentially access currently operative arrays of data in the given sector, wherein the valid arrays of data are determined based on the flag being set to an enabled state.

25. The implantable medical device of claim 18, wherein the first array of data comprises an address to at least one of a parameter, an executable code, and data stored within the plurality of sectors.

26. The implantable medical device of claim 18, wherein each of the arrays of data includes a header and the flag is contained in the header.

27. The implantable medical device of claim 26, further comprising instructions that, when executed by the microprocessor, cause the microprocessor to execute the executable code stored within the plurality of sectors.

28. The implantable medical device of claim 18, wherein each of the regions comprises a uniform number of flash memory cells.

29. The implantable medical device of claim 18, wherein each of the regions comprises a non-uniform number of flash memory cells.

30. The implantable medical device of claim 18, wherein at least one of the sectors comprises logically sequential regions.

31. The implantable medical device of claim 30, wherein the microprocessor assigns the received first array of data to a first of the logically sequential regions.

32. The implantable medical device of claim 18, wherein the flash memory array comprises at least one of NAND and NOR flash memory cells.

33. The implantable medical device of claim 18, wherein each sector of the flash memory is configured for a single write, determined based on a status of the flag on each of the regions within the sector.

34. An implantable medical device, comprising:
a microprocessor;
a flash memory array having a plurality of sectors, wherein each of the sectors includes a plurality of regions; and
a data management module comprising instructions which, when executed, by the microprocessor cause the microprocessor to:
assign a received first array of data to a first of the plurality of regions of a given one of the sectors;
store the first array of data in the assigned first region;
set a flag in the first array of data to an enabled state; and
modify the content of the flag from the enabled state to a disabled state without erasing the first region in response to a subsequent receipt of a command to update the data in the first array; and
further comprising instructions that, when executed by the microprocessor, cause the microprocessor to:
erase the contents of at least the first region of the plurality of regions prior to storing the first array of data in the assigned first region.

35. The implantable medical device of claim 34, wherein the microprocessor accesses the first array of data responsive to the flag being set to the enabled state.

36. The implantable medical device of claim 34, further comprising instructions that, when executed by the microprocessor, cause the microprocessor to:
assign a subsequently received array of data to a subsequent plurality of regions;
store the subsequently received array of data in the assigned data region; and
set a flag in the subsequently received array of data to an enabled state.

37. The implantable medical device of claim 36, further comprising instructions that, when executed by the microprocessor, cause the microprocessor to allocate one or more regions of the one or more sectors for storage of each of the received first and subsequent arrays of data.

38. The implantable medical device of claim 36, wherein the microprocessor evaluates a value of the flag in each of the first or subsequent arrays of data responsive to a memory read request, and one of: reads the data stored within any one of the arrays of data in the given sector based on the flag being set to the enabled state, and skips the data stored within any one of the arrays of data in the given sector based on a value of the flag being set to the disabled state.

39. The implantable medical device of claim 36, further comprising instructions that, when executed by the microprocessor, cause the microprocessor to set the flag of each of the plurality of sectors to a cleared state to designate each sector as not being programmed prior to storage of the first or subsequent arrays of data in each corresponding sector.

40. The implantable medical device of claim 34, further comprising instructions that, when executed by the microprocessor, cause the microprocessor to sequentially access currently operative arrays of data in the given sector, wherein the valid arrays of data are determined based on the flag being set to an enabled state.

41. The implantable medical device of claim 17, further comprising instructions that, when executed by the microprocessor, cause the microprocessor to execute the executable code stored within the plurality of sectors.

42. The implantable medical device of claim 34, wherein each of the arrays of data includes a header and the flag is contained in the header.

43. The implantable medical device of claim 34, wherein each of the regions comprises a uniform number of flash memory cells.

44. The implantable medical device of claim 34, wherein each of the regions comprises a non-uniform number of flash memory cells.

45. The implantable medical device of claim 34, wherein at least one of the sectors comprises logically sequential regions.

46. The implantable medical device of claim 34, wherein the flash memory array comprises at least one of NAND and NOR flash memory cells.

47. The implantable medical device of claim 46, wherein the microprocessor assigns the received first array of data to a first of the logically sequential regions.

48. The implantable medical device of claim 34, wherein each sector of the flash memory is configured for a single write, determined based on a status of the flag on each of the regions within the sector.

* * * * *